US008031559B2

(12) United States Patent
Lee

(10) Patent No.: US 8,031,559 B2
(45) Date of Patent: Oct. 4, 2011

(54) PULSE ALARM CLOCK WITH ALARM AND ACUPUNCTURE FUNCTIONS

(76) Inventor: Tsung Chieh Lee, Kaohsiung (TW)

( * ) Notice: Subject to any disclaimer, the term of this patent is extended or adjusted under 35 U.S.C. 154(b) by 505 days.

(21) Appl. No.: 12/244,132

(22) Filed: Oct. 2, 2008

(65) Prior Publication Data

US 2010/0085844 A1 Apr. 8, 2010

(51) Int. Cl.

| | |
|---|---|
| ***G04B 47/00*** | (2006.01) |
| ***G04B 23/02*** | (2006.01) |
| ***A61N 1/00*** | (2006.01) |

(52) U.S. Cl. .............. 368/10; 368/73; 368/230; 607/46; 607/72

(58) Field of Classification Search .................... 368/10, 368/12, 73, 24, 230, 250; 607/46, 72
See application file for complete search history.

(56) References Cited

U.S. PATENT DOCUMENTS

| | | | | |
|---|---|---|---|---|
| 4,432,653 | A * | 2/1984 | Ting-Ching | 368/250 |
| 4,981,146 | A * | 1/1991 | Bertolucci | 607/72 |
| 5,563,850 | A * | 10/1996 | Hanapole | 368/89 |
| 6,594,202 | B1 * | 7/2003 | Ting | 368/230 |
| 2003/0195585 | A1 * | 10/2003 | Gruzdowich et al. | 607/45 |
| 2006/0015154 | A1 * | 1/2006 | Zou et al. | 607/46 |
| 2008/0071329 | A1 * | 3/2008 | Giuntoli et al. | 607/72 |
| 2011/0082515 | A1 * | 4/2011 | Libbus et al. | 607/44 |

* cited by examiner

*Primary Examiner* — Vit Miska
(74) *Attorney, Agent, or Firm* — Ming Chow; Sinorica, LLC

(57) ABSTRACT

The present invention relates to a pulse alarm clock consisting of a main body of the alarm clock and two quick-fastening straps, wherein it has a high-voltage pulse generator installed inside the main body of the alarm clock, which is controlled by a timing device therefrom, and in addition, both its positive and negative pulse electrodes, which are controlled by a transfer switch, are extending outward along with an output-end and then combining all together at two quick-fastening straps, and thereat, it is able to fasten the alarm clock at a high sensitive portion of a human body with the utilization of these two quick-fastening straps, thereby, when it is reaching the preset alarm time on the alarm clock, it will activate the high-voltage pulse generator to creating the vibration effect that will be transferred to a high sensitive portion of the human body through these two quick-fastening straps and thus achieving the objective of wakening the user from sleep consequently.

1 Claim, 5 Drawing Sheets

PULSE ALARM CLOCK WITH ALARM AND ACUPUNCTURE FUNCTIONS

BACKGROUND OF THE INVENTION

1. Field of the Invention

The present invention relates to a pulse alarm clock, particularly to a kind of pulse alarm clock which is able to perform either the effect of acupuncture on the acupuncture point or the alarm effect in wakening the user from sleep accordingly.

2. The Prior Arts

Currently the alarm clocks sold on the market generally have two kinds of ringing methods, i.e. the alarm tone and music tone, in which, the ringing method of alarm tone is sounded by hitting the bell-jar continuously with a ram, and thereat, the audio frequency sounded is too harsh and loud to the ears and is very easily disturbing the other people staying in the same area; and instead, although the low frequency music tone is more gentle which will not disturb the other people if comparing to the alarm tone, but it might not waken up the user while she/he was too sleepy, therefore, it is obviously that both ringing methods used for the current alarm clocks are not the perfect designing method for the alarm clock.

SUMMARY OF THE INVENTION

The primary objective of the present invention lies in providing a pulse alarm clock which comprises a pulse generator controlled by a timing device of the said alarm clock, wherein two signal transmission lines are extending outward and being combined at two quick-fastening straps, and thereat, it is able to fasten the said alarm clock at a high sensitive portion of a human body with these two quick-fastening straps, thereby, when it is reaching the preset alarm time on the said alarm clock, it will activate the high-voltage pulse generator to transmitting pulse signals to the positive and negative pulse electrodes through two signal transmission lines in order to acting the effect of acupuncture on the acupuncture point thereto, or instead transmitting pulse signals to the output-end to stimulating a high sensitive portion of the human body and hence wakening the user from sleep without disturbing other people at all. Another objective of the present invention is to provide a kind of pulse alarm clock having a transfer switch installed inside the clock, thereby, the transmitting pulse signals generated by the high-voltage pulse generator will be further converted into either the positive or negative pulse electrode or even just a single signal in order to perform the effect of acupuncture on the acupuncture point thereto or instead the alarm effect in wakening the user from sleep accordingly.

BRIEF DESCRIPTION OF THE DRAWINGS

The present invention will be apparent to those skilled in the art by reading the following detailed description of a preferred embodiment thereof, with reference to the attached drawings, in which.

DETAILED DESCRIPTION OF THE PREFERRED EMBODIMENT

Figure 1:
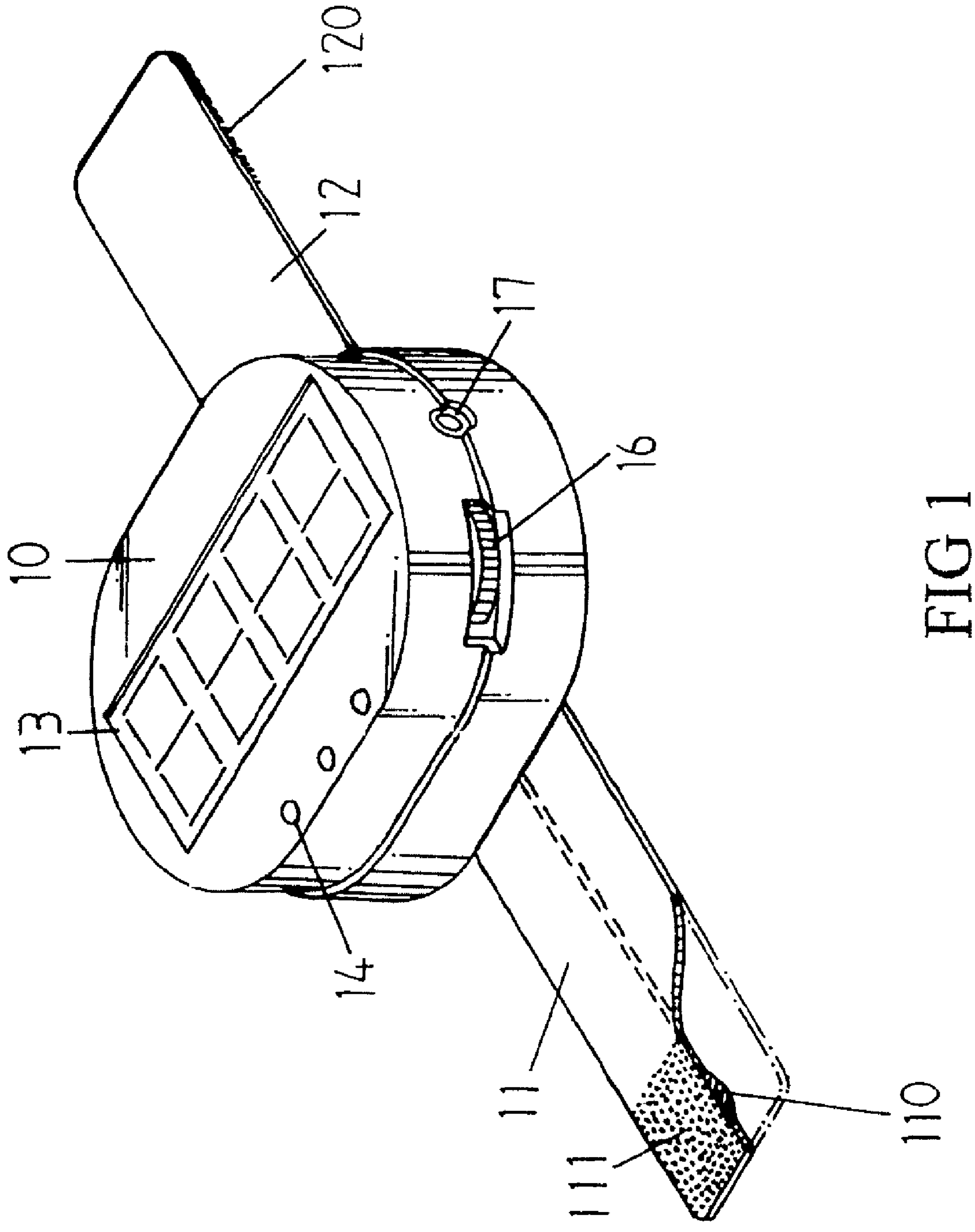
FIG. 1 is a stereoscopic view of structure in accordance with the present invention.
Figure 2:
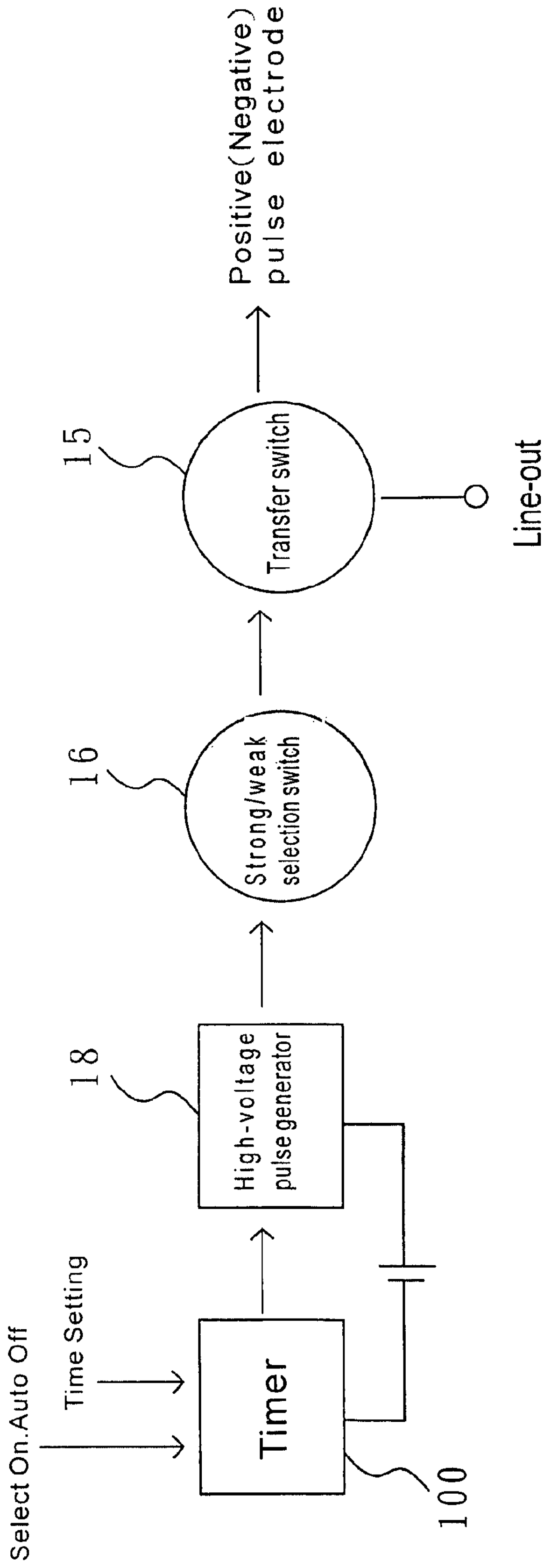
FIG. 2 is a block diagram showing the electrical circuit according to the present invention.

According to FIGS. 1 and 2, the present invention consists of a main body 10 of the alarm clock and two quick-fastening straps 11, 12, wherein a time display 13 and a plurality of push buttons 14 used for setting alarm times are installed at the top of the main body 10 of the said alarm clock, and moreover, locating at one side of the main body 10 of the said alarm clock, it is respectively equipped with one transfer switch 15, one strong/weak selection switch 16 and one switchover socket 17, which is connecting with a transfer switch 15; and furthermore, a high-voltage pulse generator 18 installed inside the main body 10 of the said alarm clock, which is controlled by a timing device 100 therefrom; where the said high-voltage pulse generator 18 is connected with the strong/weak selection switch 16 and the transfer switch 15, and thereat, the said transfer switch 15 is being used to transmit either a single signal 192 or the positive (negative) pulse electrode 191 to the said two quick-fastening straps 11, 12 through the transmitting lines 19.

Figure 3:
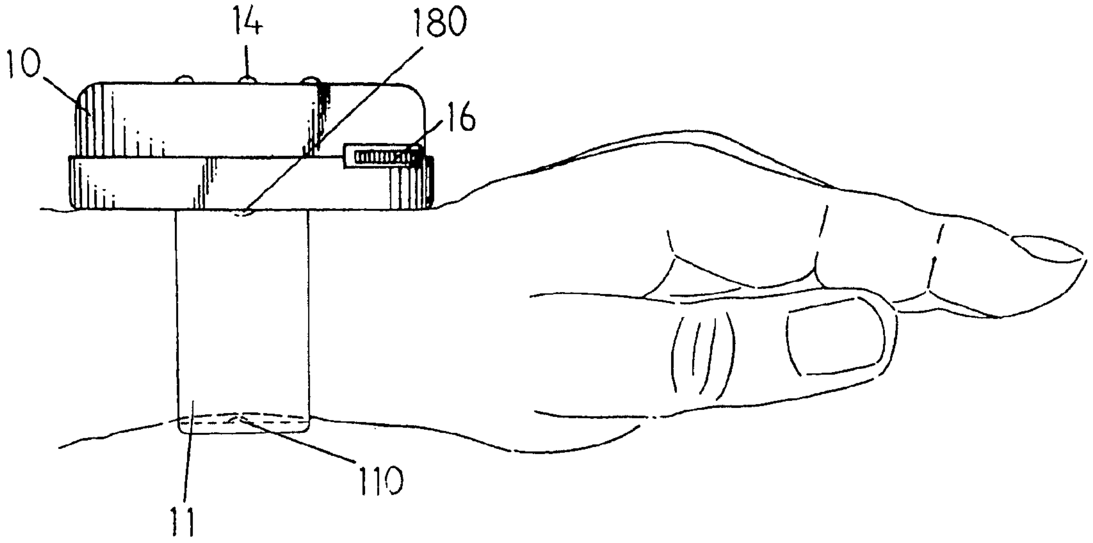
FIG. 3 is a schematic view showing the present invention is being worn on the wrist of a user.
Figure 4:
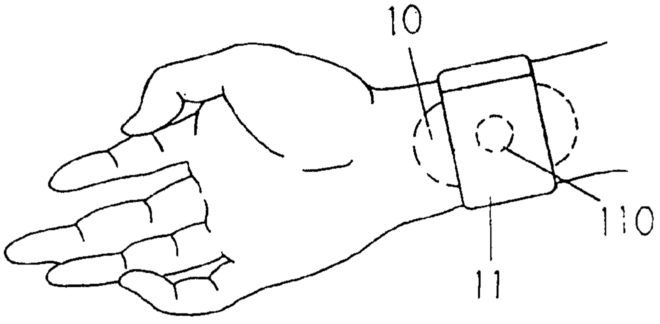
FIG. 4 is a schematic view showing the completion of wearing the present invention.
Figure 5:
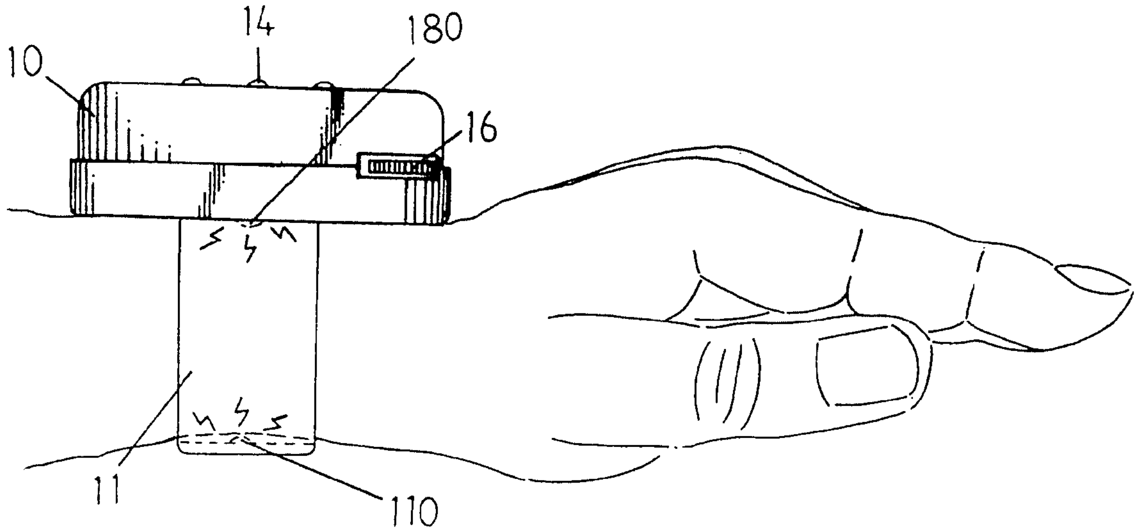
FIG. 5 is a schematic view showing the vibrating condition of the present invention.
Figure 6:
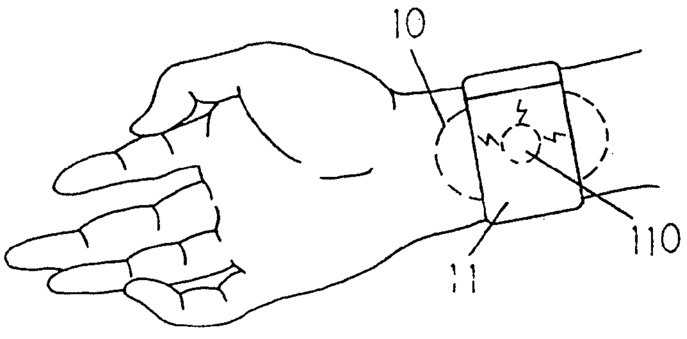
FIG. 6 is a schematic view showing the sensing condition of the present invention.

With reference to FIGS. 3 and 4, it is shown that when a sleeping user would like to waken her/him up at the preset alarm time with the said alarm clock, she/he can utilizes two quick-fastening straps 11, 12, to fasten the main body 10 of the said alarm clock at a sensitive portion of the human body (e.g. the wrist portion as shown in the related figures), and then using the push buttons 14 to preset preferable alarm times; when it is reaching the preset alarm time, the signals generated inside the main body 10 of the said alarm clock will activate the high-voltage pulse generator 18 generating the pulse signals which will be transmitted as a single signal 192 through the transmitting line 19 in the said quick-fastening straps 11, 12, and furthermore the said quick-fastening straps will then simulate the sensitive portion and hence wakening the sleeper accordingly (as shown in FIGS. 5 and 6).

Figure 7:
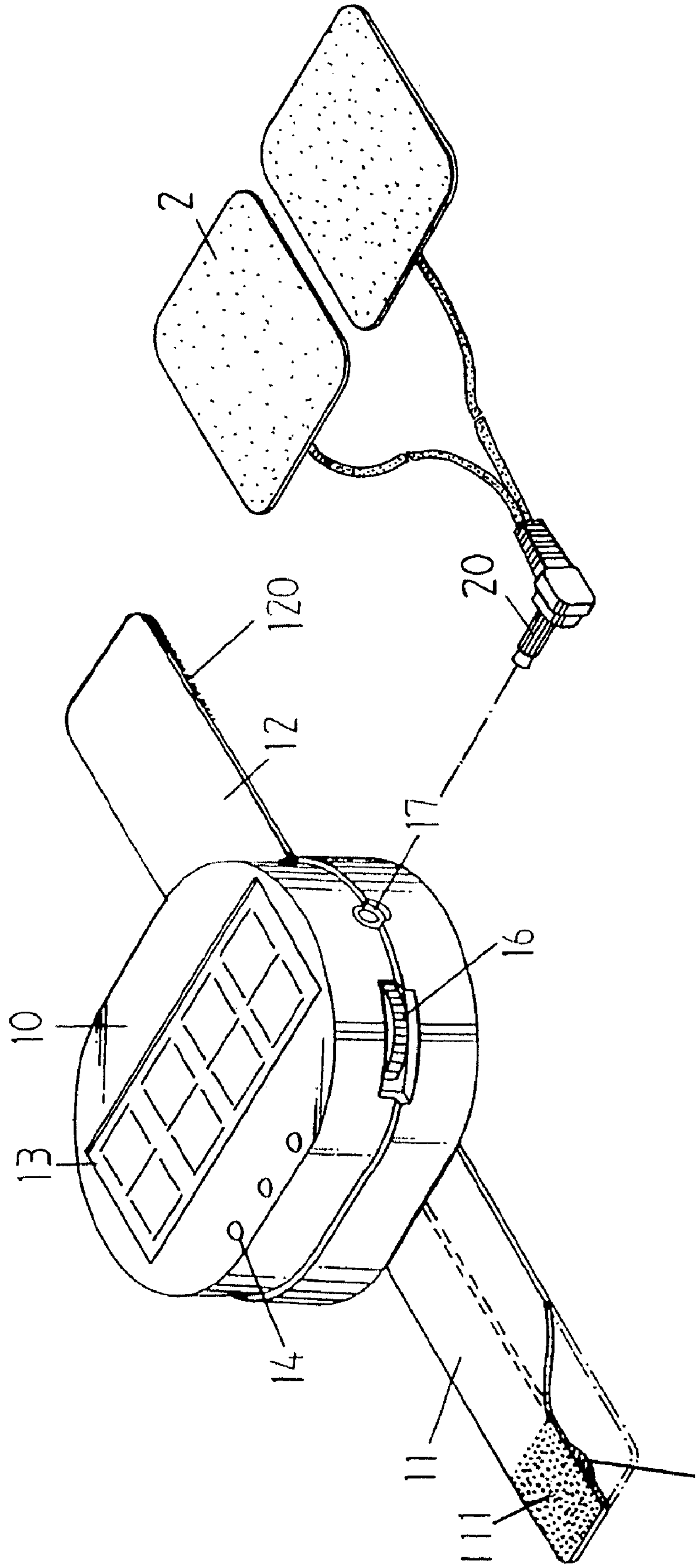
FIG. 7 is a schematic view showing the other functionability in accordance with the present invention.

If it is not necessary for the sleeper to use the alarm clock function, then instead she/he can plug-in the electrode patch 2 into the switchover socket 17 with an insert 20, meanwhile utilizing the transfer switch to convert the signals generated by the high-voltage pulse generator from a single signal 192 into the positive (negative) pulse electrode 191, and thereat, while the electrode patch 2, which is adhered to a sensitive portion of the human body, is receiving the signals transmitted by the positive (negative) pulse electrode, the said electrode patch 2 will be able to provide the effects of human body's acupuncture points (as shown in FIG. 7).

Although the present invention has been described with reference to the preferred embodiment thereof, it is apparent to those skilled in the art that a variety of modifications and changes may be made without departing from the scope of the present invention which is intended to be defined by the appended claims.

What is claimed is:

1. A pulse alarm clock comprising:

a main body connecting to two quick-fastening straps;

a time display and a plurality of push buttons used for setting alarm times being installed at the top of the main body of the pulse alarm clock;

a transfer switch, a strong/weak selection switch and a switchover socket being equipped at one side of the main body of the pulse alarm clock respectively;

a high-voltage pulse generator being installed inside the main body of the pulse alarm clock and being controlled by a timing device therefrom;

the said-high-voltage pulse generator being connected with the transfer switch;

the transfer switch being used to switch over pulse signals generated by the high-voltage pulse into either a single signal or a positive (negative) pulse electrode;

the two quick-fastening straps being used to fasten the main body of the pulse alarm clock at a positive portion of a human body;

a transmission line being installed inside the two quick-fastening straps respectively, in order to receive output signals, generated by the high-voltage pulse generator and transmit the output signals to a sensitive portion of the human body; and the switchover socket being plugged-in with an acupuncture point massager in order to achieve the effect of acupuncture point massage.

* * * * *